(12) United States Patent
Görz et al.

(10) Patent No.: US 11,931,476 B2
(45) Date of Patent: Mar. 19, 2024

(54) METHOD FOR PRODUCING A STERILIZABLE STRAINER DISH HAVING A THREE-DIMENSIONALLY STRUCTURED BOTTOM

(71) Applicant: Aesculap AG, Tuttlingen (DE)

(72) Inventors: Dennis Görz, Tuttlingen (DE); Bianca Rosin, Tuttlingen (DE); Eva Streit, Bodman-Ludwigshafen (DE); Timo Knittel, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 853 days.

(21) Appl. No.: 16/978,268

(22) PCT Filed: Mar. 1, 2019

(86) PCT No.: PCT/EP2019/055183
§ 371 (c)(1),
(2) Date: Sep. 4, 2020

(87) PCT Pub. No.: WO2019/170551
PCT Pub. Date: Sep. 12, 2019

(65) Prior Publication Data
US 2021/0008240 A1      Jan. 14, 2021

(30) Foreign Application Priority Data
Mar. 5, 2018  (DE) .................. 10 2018 104 939.0

(51) Int. Cl.
*A61L 2/26*     (2006.01)
*A61B 50/20*    (2016.01)
*A61B 50/34*    (2016.01)

(52) U.S. Cl.
CPC ............... *A61L 2/26* (2013.01); *A61B 50/20* (2016.02); *A61B 50/34* (2016.02); *A61L 2202/17* (2013.01); *A61L 2202/24* (2013.01)

(58) Field of Classification Search
CPC .......... A61B 50/20; A61B 50/22; A61B 50/30
See application file for complete search history.

(56) References Cited

U.S. PATENT DOCUMENTS 5,183,643 A     2/1993  Nichols
8,042,369 B2 *  10/2011 Bytow ................. B21D 19/005
                                              29/90.01
(Continued)

FOREIGN PATENT DOCUMENTS

CN    101818554 A    9/2010
CN    101947512 A    1/2011
(Continued)

OTHER PUBLICATIONS

DE-202005006125-U1 English translation (Year: 2005).*
(Continued)

*Primary Examiner* — Jason L Vaughan
*Assistant Examiner* — Amanda Kreiling
(74) *Attorney, Agent, or Firm* — Christopher A. Rothe; Culhane Meadows PLLC

(57) ABSTRACT

A method for producing a strainer dish for receiving medical objects to be disinfected or sterilized. A base surface is produced from a sheet metal blank in a first machining step. In a second machining step, the sheet metal blank or base surface is provided with holes to obtain a perforated starting shape. In a third machining step which takes place after the first and second machining steps, a perforated plane is produced, which can be divided into a flat inner section and an edge section. In a fourth machining step which takes place after the third machining step, a strainer dish shape is produced. The raw bottom corresponds to the flat inner section of the perforated plane. A fifth machining step, (Continued)

which takes place after the third machining step, at least partially produces a three-dimensionally structured bottom from the flat inner section.

21 Claims, 7 Drawing Sheets

(56) References Cited

U.S. PATENT DOCUMENTS

| | | | |
|---|---|---|---|
| 10,058,230 B2 | 8/2018 | Gobl | |
| 10,427,386 B2 | 10/2019 | Demange et al. | |

FOREIGN PATENT DOCUMENTS

| | | | | |
|---|---|---|---|---|
| CN | 202606648 U | | 12/2012 | |
| CN | 203792726 U | | 8/2014 | |
| CN | 106388299 A | | 2/2017 | |
| DE | 10124253 A1 | * | 12/2002 | ............. A61B 50/20 |
| DE | 202005006125 U1 | * | 8/2005 | ............. A61B 50/20 |
| DE | 10124253 | | 12/2005 | |
| DE | 202006011942 U1 | | 10/2006 | |
| DE | 102008055021 A1 | | 6/2010 | |
| DE | 102010050919 A1 | * | 5/2012 | ............. A61L 2/26 |
| DE | 102010050919 A1 | | 5/2012 | |
| DE | 102013002458 A1 | | 8/2014 | |
| DE | 102016123864 A1 | | 6/2018 | |

OTHER PUBLICATIONS

DE-102010050919-A1 English translation (Year: 2012).*
DE-10124253-A1 English translation (Year: 2002).*
German Search Report received in Application No. 10 2018 104 939.0 dated Oct. 23, 2018, 11 pages. (with translation).
International Search Report received in PCT/EP2019/055183 dated Mar. 1, 2019, 7 pages. (with translation).
Office Action received in Chinese Application No. 201980015899.5 dated Jan. 13, 2022, with translation, 23 pages.
Office Action received in Chinese Application No. 201980015899.5 dated Jun. 14, 2022, with translation, 34 pages.

* cited by examiner

METHOD FOR PRODUCING A STERILIZABLE STRAINER DISH HAVING A THREE-DIMENSIONALLY STRUCTURED BOTTOM

CROSS-REFERENCE TO RELATED APPLICATION(S)

This application is the United States national phase entry of International Application No. PCT/EP2019/055183, filed Mar. 1, 2019, which claims the benefit of priority of German Application No. 10 2018 104 939.0, filed Mar. 5, 2018. The contents of International Application No. PCT/EP2019/055183 and German Application No. 10 2018 104 939.0 are incorporated by reference herein in their entireties.

FIELD

The present invention relates to a method for producing a sterilization sieve tray, also called sieve basket, such as a sterilization or disinfection sieve basket, for storing medical items to be disinfected or sterilized. Generic sieve baskets are used to provide a portable receiving container in a cleaning and disinfection device (CDD) or autoclave in a processing unit for medical devices (PUMD) for a number of items to be disinfected or sterilized, such as surgical gripping instruments.

BACKGROUND

The primary function of a sieve basket is to hold several items in its sieve basket interior, so that they can be handled as a single unit during the cleaning process. Furthermore, the stored items must be prevented from slipping or sliding during the packing process—in the interests of compact loading of the sieve basket.

Furthermore, a sieve basket should have as few sections as possible or none at all in which cleaning liquid (i.e. water with additives) used during the cleaning process accumulates, so that the used cleaning liquid is drained/drips off the sieve basket as completely as possible after the cleaning process.

Finally, it is important to ensure that sieve baskets do not have any sections susceptible to breakage or cracking even after intensive use, during which they are exposed to impact and cutting loads, thus minimizing the risk of injury or cutting for an operator.

From DE 20 2006 011 942 U1, a sieve basket is known, which is adapted to accommodate items to be disinfected or sterilized. The sieve basket has a bottom, in particular a sheet metal base, which is provided with a plurality of apertures. The bottom has a base plane bounded by side walls which is produced in a forming step.

This base plane is designed flat as a kind of perforated metal plate. In order to prevent the stored items from slipping or sliding, a mat is inserted into the sieve basket. This mat prevents the sieve basket from being drained efficiently so that even after the sieve basket has been removed from the CDD, residual water causes interfering moistening of various sieve basket areas, in particular of the sieve basket bottom.

The problem of interfering moistening of the sieve basket bottom still exists even if the mat is not inserted. The flat base plane has the effect that a surface contact is formed between the items stored in the sieve basket and the bottom, corresponding to the remaining web widths between the plate holes, at which residual water accumulates under capillary action, which in turn promotes interfering moistening.

Another genre of sieve baskets of the prior art is designed as a wire mesh instead of a perforated metal plate. A wire mesh has a grooved base plane that prevents the stored items from slipping or sliding away. Furthermore, a wire mesh causes less surface contact, for example with a flat ground, and consequently less capillary action.

The disadvantage of sieve basket wire meshes is, however, that not only residual water but also dirt accumulates in the individual junctions of the meshwork. Furthermore, after a certain period of use, the individual wires in a wire mesh will inevitably break or become detached, which considerably increases the risk of injury posed by a sieve basket wire mesh.

Furthermore, in a sieve basket wire mesh, the wall perforation corresponds to the bottom perforation. If the wire mesh is woven sufficiently coarsely in order to prevent the stored items from slipping or sliding on the base plane, it has the disadvantage that the wall perforation is so wide that the stored items can project through it, which again increases the risk of injury and makes handling more difficult.

Ultimately, a wire-mesh sieve basket is also more complex to produce, since it is not based on a low-cost sheet metal as the basic material.

Thus, the sieve baskets and their production methods from the prior art all have the disadvantage that even after removal from the CDD they still moisten other surfaces in a non-desirable way due to adhering residual water. Depending on their design, they also have the disadvantage of an increased risk of injury, the disadvantage of the stored items slipping or sliding away, and/or the disadvantage of pollution or accumulation of germs. Moreover, their production methods are overall less technically mature.

SUMMARY

In view of this prior art, the present invention is based on the object of eliminating or at least reducing the disadvantages of the prior art, and in particular to disclose an efficient production method that allows economic mass production of sieve baskets that drip off quickly, can be loaded compactly, and which pose a low risk of injury.

It has been found that the formation or arrangement of spacer feet/knobs, for example on the outside/underside of a flat perforated plate processed to form a sieve basket bottom, may reduce the contact area between the sieve basket and a flat ground and thus could improve the overall drip-off behavior, but the production of such a special plate would be complex and expensive and thus uneconomic overall. In addition, the spacer feet/knobs would be distributed over the plate surface with a certain distance between each other, which could therefore possibly bend depending on the distance selected between two adjacent spacer feet/knobs. For these reasons, such a solution to the problem stated at the beginning has not proven to be effective.

The basic idea of the present invention now pursues the basic concept of simulating the spatial structure of a wire mesh in an initially planar perforated plate by deforming the webs extending (and crossing) between the plate holes (pores) at least partially or in sections in one or more directions different from their respective web-extension direction, whereby the deformed webs themselves at least partially define point-like contact areas, for example with a planar ground. This makes it possible to form/retrofit virtually any initially flat perforated plate with this additional capability, i.e. the provision of almost any selectable number of point-like contact areas in the form of correspondingly three-dimensionally extending plate webs between the plate holes, for example by subjecting the initially flat perforated plate to a corresponding (final) deformation step.

In the context of this application, the term 'perforated plate' is understood to mean a plate extending in two principal directions in space, preferably made of sheet-metal material with a constant thickness/material strength of the sheet metal in a third sub-direction. By the formation of corrugations or indentations/bulges, in particular in the third sub-direction, the perforated plate is additionally given a three-dimensional, varying structure which deviates from the flat plate with the constant plate thickness/plate strength. It is advantageous not to form the indentations/bulges in the macro range, i.e. to form a single indentation/bulge over a plurality/number of webs, but to provide the indentations/bulges in the micro range, i.e. to form the respective indentation/bulge, for example, essentially within/along the respective web (preferably between two or three intersection points/nodes with the respective other webs) and/or at a selected junction (area within a number of junctions directly surrounding a single junction in the form of a circle as the middle and thus contact point).

The following additional advantages can be derived from this method of producing a three-dimensional perforated plate according to the invention:

- The method can be automated, which minimizes production costs, in particular for the targeted large series.
- Surfaces with which the sieve basket produced according to the invention comes into contact after being removed from the CDD are not moistened by the CDD or are considerably less moistened.
- By using a sheet metal blank, a wire mesh is not required, which reduces the manufacturing costs and also eliminates the risk of punctures on the produced sieve basket.
- The perforation geometry of the bottom can be designed independently of the side walls by the separation or punching step, so that they are adapted to different requirements.
- The stored items can also be prevented from slipping or sliding off without inserting a (silicone) mat.

According to the invention, at least the bottom of the sieve basket has or consists of a perforated plate preferably as sheet metal part which has/receives, preferably periodic, three-dimensional corrugations or indentations, also dents/convexities or depressions, which project from the base plane initially formed by the flat perforated plate towards the sieve basket interior/inwards and/or towards the sieve basket exterior/outwards, so that the perforated plate bottom or sheet metal bottom has/receives a surface in the manner of a (wire) meshwork. Thus, a perforated plate/sheet metal part imitates/simulates/reproduces or replicates a meshwork surface structure, whereby the structure of a meshwork and that of a perforated metal plate are synergistically combined with each other. Preferably, at least the sheet metal part or the perforated plate of at least the sieve basket bottom has/receives a number of through holes (pores), which are circumferentially defined by overlapping/crossing webs and are spaced from each other according to the web width. In accordance with the invention, deformations (bulges/teeth) in one or more directions different from their respective web-extension direction, in particular (alternately) in the direction of the outside and/or inside of the sieve basket are formed in/on individual webs, resulting in a rough/teethed bearing surface on the bottom outside and/or a rough/teethed bearing surface on the bottom inside.

In order to produce such a three-dimensional perforated plate, the subject matter of the invention thus relates to a method of producing such a perforated plate and a sieve basket provided with this perforated plate for receiving medical items to be disinfected or sterilized. In the method, the following steps (not necessarily chronologically) are carried out based on a plate blank, in particular a sheet-metal blank:

1. a first processing step, preferably separating, especially preferably nibbling or cutting, such as laser or water jet cutting, produces a plane sieve basket base surface from the plate blank or sheet-metal blank, consisting of the (later) sieve basket bottom and the (later) sieve basket side walls;
2. a second processing step (taking place prior to or after the first processing step), preferably separating, especially preferably punching, provides the sheet-metal blank or the sieve basket-base surface with apertures/holes/pores, in particular in the area of the (later) sieve basket bottom and optionally in selected/selectable areas of the (later) sieve basket side walls, if desired with holes of sizes different from the sieve basket bottom, in order to obtain a perforated initial shape;
3. subsequently, optionally a third processing step (taking place after the first and the second processing step), preferably forming, especially preferably rolling/'smoothing', produces a perforated plane. (This step is necessary, since during the first and/or the second processing step deformation/warping occurs within the sheet metal, which is caused by internal stress, for example);
4. a fourth processing step (which takes place after the third processing step), preferably forming, especially preferably bending/beveling the side wall area relative to the bottom region, produces a sieve basket (basic) shape, the raw bottom of which corresponds to the flat inner portions of the perforated plane and the side walls correspond to the flat outer portions of the perforated plane.

On the basis of a sheet metal that is cheap to acquire and easy to process by cutting, punching and bending, a basic sieve basket shape can be produced in just a few steps, which (after welding the side walls together) would theoretically already be suitable for use in a CDD.

According to the invention, a fifth processing step is provided (after the third processing step, but not necessarily after the fourth processing step), preferably forming, especially preferably embossing, which at least partially results in a three-dimensionally structured bottom with the preceding structure at least from the flat inner portion (which defines the sieve basket bottom). In this way, the previously flat bottom of the sieve basket is provided with a grooved structure, without deformations occurring during the fifth processing step/embossing in other areas of the sieve basket not intended for embossing deformation.

In other words, the invention can be functionally described in such a way that a sieve basket with a bottom is produced of sheet metal, said bottom has/simulates the surface geometry and structure of a meshwork, but without being woven. Thus, the invention has the effect of realizing the advantages of a meshwork (bottom structure with contact and fixation surfaces, efficient dripping) without its disadvantages (see below). Weaving means that two interlaced strands/wires overlap/lie on top of each other in the junctions. For sieve baskets, such overlapping is associated with the considerable disadvantage that germs and dirt particles accumulate in the overlapping point, i.e. the junction, as these are difficult to reach and therefore difficult to clean. Moreover, meshwork production is significantly more difficult than sheet metal processing. These disadvantages of the prior art are efficiently eliminated by the 'meshwork simulation' according to the invention.

The inventive idea, therefore, is that the production of a mesh-like/mesh-simulated bottom sheet metal prevents the items to be cleaned from slipping away during the packing process of the sieve basket on the one hand, while on the other hand the presence of residual water in the sieve basket after the cleaning process in the CDD is reduced or even prevented, so that there is no interfering moistening (of the packing table, for example).

In this context, it should be noted that the processing steps described in this application may each comprise several sub-steps.

In an advantageous embodiment of the invention, the fifth processing step/embossing takes place prior to the fourth processing step. In this case, the embossing of the three-dimensional structure takes place immediately after smoothing of the base plate/workpiece being cut into the inner and outer areas and having been perforated, whereby the base plate/workpiece thus partially processed still has a low height during embossing (because no side walls are yet bent), so that an embossing tool used only needs to be moved slightly in the height direction. In this case, it would also be possible to correspondingly emboss the outer areas of the base plate that are intended as side walls.

As an alternative to this embodiment, the processing steps from the first processing step to the fifth processing step can be executed chronologically in exactly this order. Thus, the cut and already perforated sheet metal part is bent into a sieve basket with side walls extending perpendicularly from the bottom, before the bottom is embossed (fifth step) to create the three-dimensional structure as defined above. This procedure then has the advantage that production methods from the prior art can be converted in such a way that the fifth processing step according to the invention is to be carried out subsequently to the previous method or existing sieve baskets made of perforated sheet metal can be retrofitted with a corresponding three-dimensional structure.

Preferably, a sixth processing step is carried out after the fourth processing step, preferably (e.g. positive substance) joining, especially preferably welding, such as fusion joint welding, which firmly connects the individual edge portions, which now form side walls of the sieve basket, with each other at the edges. The fifth processing step can be carried out either prior to or after the sixth processing step. The sixth processing step guarantees a robust construction of the sieve basket.

A further advantageous embodiment is characterized by the fact that the apertures/holes obtained in the second processing step/punching produce differently structured perforations in the flat inner portion and the outer or edge portion. Thus, the punching tool has differently designed or selectable active surfaces distributed over the base surface for such structuring.

Advantageously, in the fifth processing step/embossing, at least one punch is used, in the manner of an embossing punch, which is pressed by a press onto a part of at least the flat inner portion (hereinafter referred to as the sieve basket bottom) of the already cut and perforated base plate in such a way that the part of the inner portion fits plastically to the negative form of the punch. In this way, the desired three-dimensional structure can be produced with high precision.

Further advantageously, a large number of punches is used in this punching step, so that the entire flat inner portion is designed as a three-dimensionally structured base. Further preferably, the corresponding punches have the same structure, so that the flat inner portion is uniformly deformed. The fact that the entire inner portion in this embodiment is designed as a three-dimensionally structured base, means that the sieve basket drains quickly (as mentioned at the beginning) and brings about the associated advantages.

In a preferred embodiment, the punch has such a shape/design that the three-dimensionally structured bottom produced in the fifth processing step has (periodic) corrugations or indentations which protrude towards the sieve basket interior and/or towards the sieve basket exterior, so that the bottom has a meshwork type surface. This meshwork simulation combines the advantages of sheet metal sieve baskets with wire sieve baskets in a synergistic way.

A further advantageous embodiment is distinguished by the fact that the punch is designed in such a way that the three-dimensionally structured bottom produced in the fifth processing step is composed of a plurality of, in the base plane parallel, longitudinal strut pairs/longitudinal web pairs and transverse strut pairs/transverse web pairs running perpendicular to each other in a plan view of the structured bottom. Thus, the fifth processing step deforms the bottom exclusively in the sieve basket height direction, i.e. towards the sieve basket interior and/or the sieve basket exterior, while a grid structure advantageous for packing is retained in the plan view.

The punch used in the method according to the invention is further preferably designed in such a way that the three-dimensionally structured bottom forms contact and fixing surfaces for items to be placed in the sieve basket. In this way, the positional stability of the stored items is increased and there is no need to place a (silicone) mat on the bottom in order to ensure that the individual items adhere securely and form-fittingly.

BRIEF DESCRIPTION OF THE DRAWING FIGURES

The invention is explained in more detail in the following on the basis of preferred embodiments with reference to the accompanying figures. The figures are merely schematic in nature and serve exclusively to understand the invention. The same elements are marked with the same reference signs.

DETAILED DESCRIPTION

Figure 1:
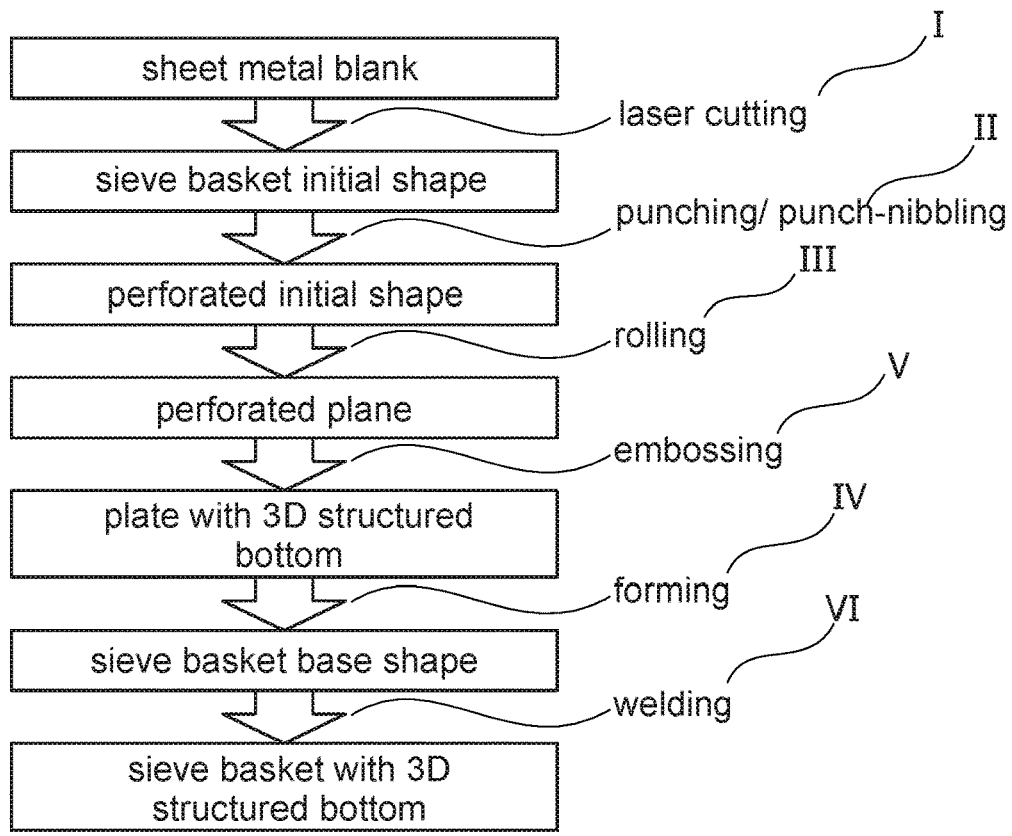
FIG. 1 shows a flow chart of the production method according to the invention.
Figure 7:
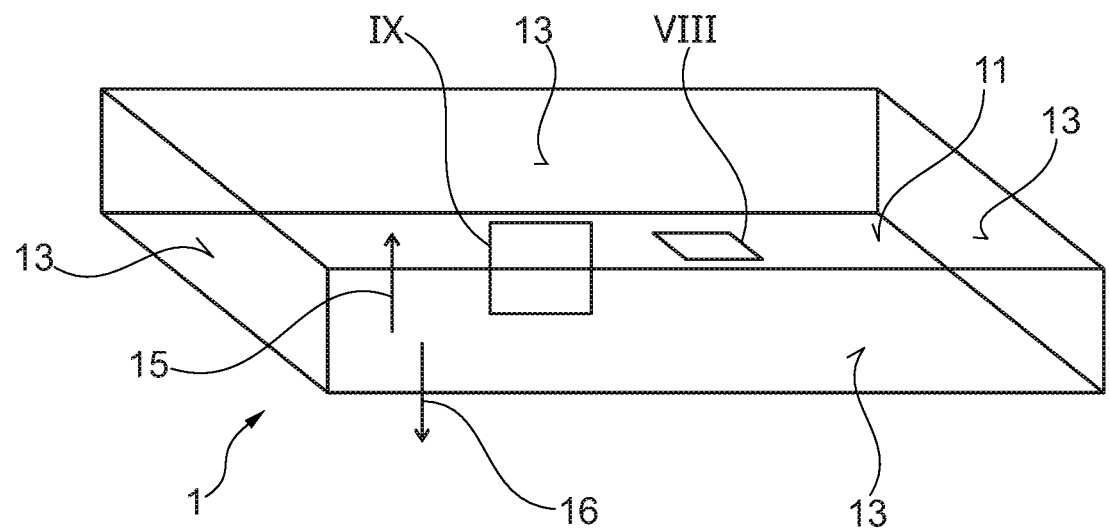
FIG. 7 shows a perspective view of a sieve basket.

FIG. 1 chronologically shows a first possibility of a method sequence for producing a sieve basket 1 (see FIG. 7). Here, laser cutting I, punching II (also punch-nibbling, provided that the part to be punched is only partially punched and partially broken), rolling III, embossing V, bending IV, and welding VI are carried out chronologically one after the other.

Figure 2:
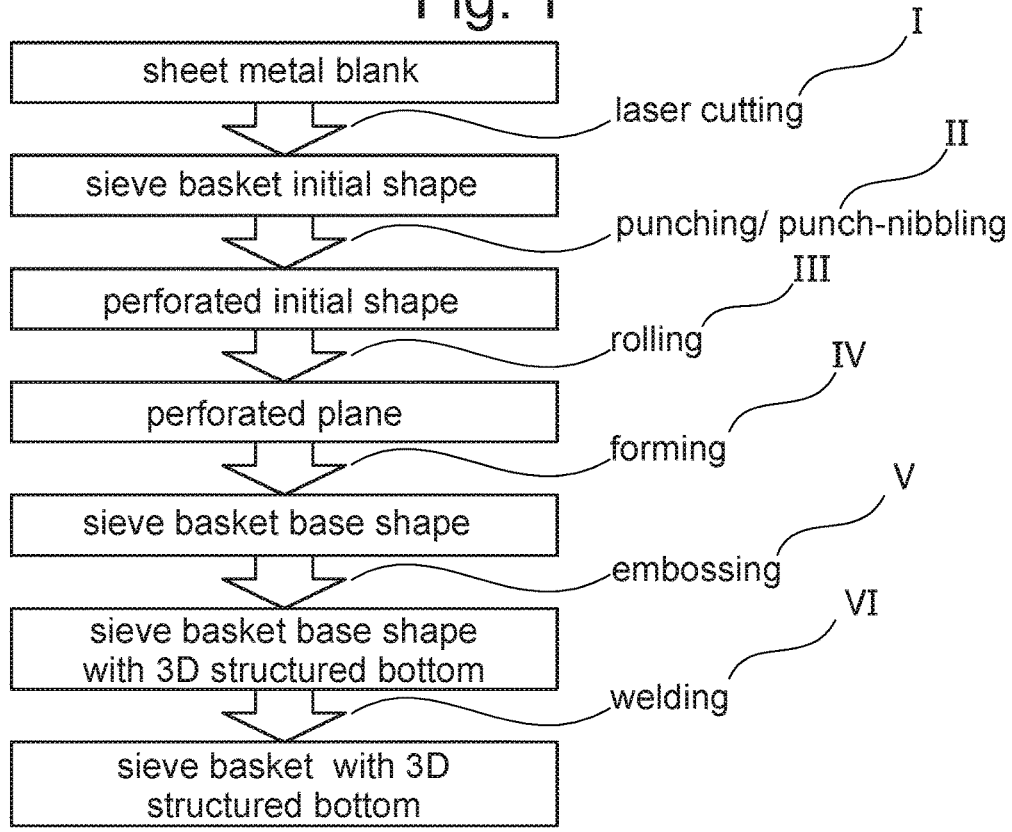
FIG. 2 shows a further flow chart of the production method according to the invention.

FIG. 2 shows a second possibility of a chronological method sequence. Here, laser cutting I, punching II (also punch-nibbling, provided that the part to be punched is only partially punched and partially broken), rolling III, bending IV, embossing V, and welding VI are carried out chronologically one after the other.

The components resulting after each step, which are already stated in the boxes of FIGS. 1 and 2, are now explained in more detail in connection with FIGS. 3 to 7.

Figure 3:
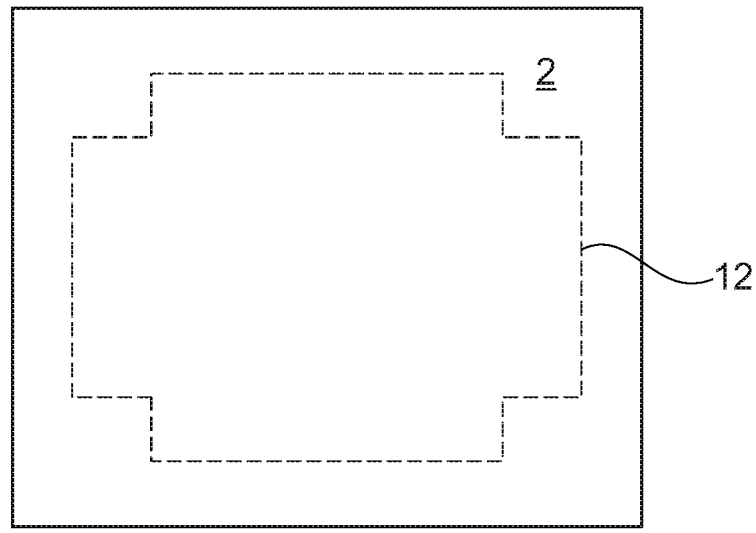
FIG. 3 shows a sheet metal blank being the basis of the production method.

In FIG. 3, a rectangular sheet-metal blank 2 is shown. This can have any shape. Its material thickness is around 0.5 mm to 2 mm, preferably around 1.5 mm. FIG. 3 already indicates a cutting contour 12 along which the laser cutting I is performed.

Figure 4:
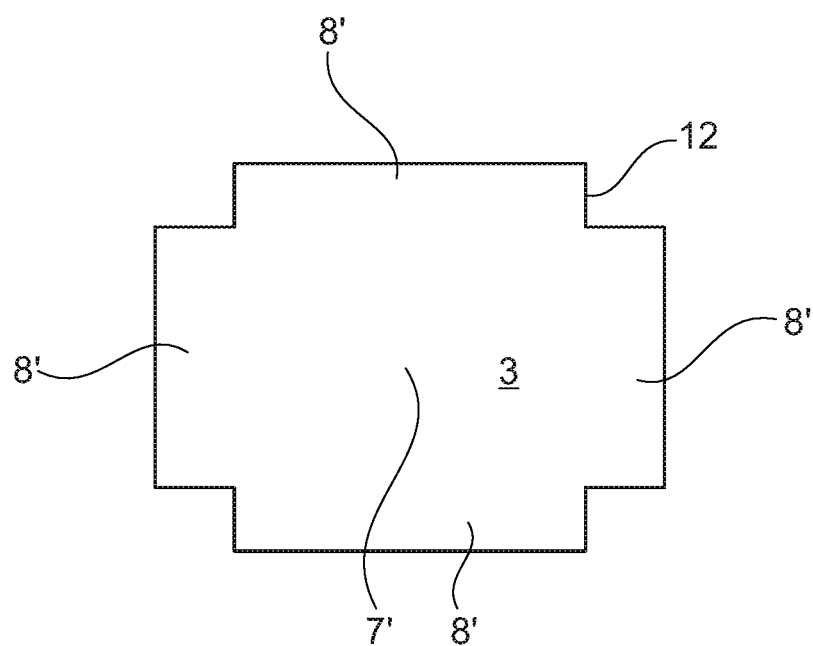
FIG. 4 shows a sieve basket-initial shape produced from the sheet metal blank of FIG. 3.

FIG. 4 shows a sieve basket base surface 3, which was cut out of the sheet-metal blank 2 along the cutting contour 12. The sieve basket-base surface 3 already has areas 7' and 8', which are modified to form a flat inner portion 7 or edge portions 8 after further processing (see FIG. 5).

Figure 5:
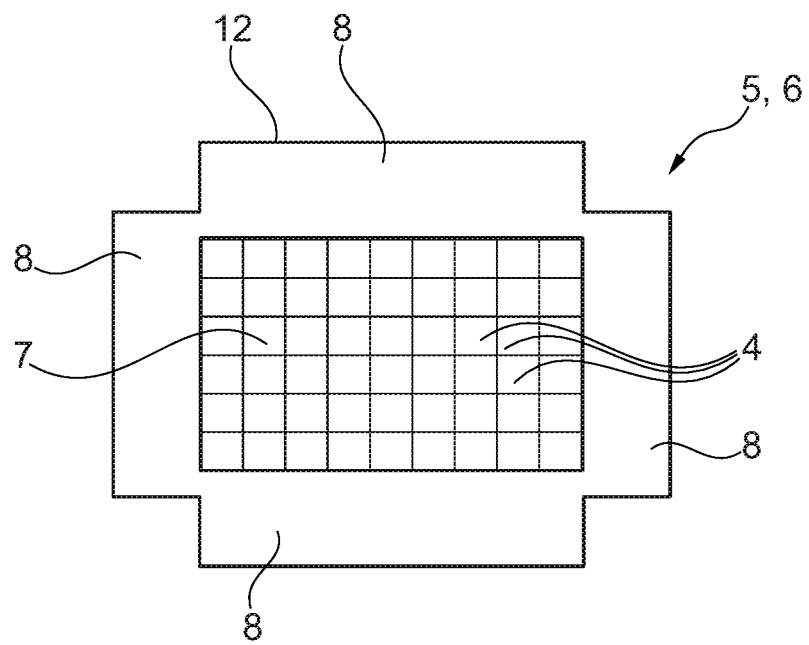
FIG. 5 shows a perforated initial shape (when rolling has not yet taken place) or a perforated plane (when rolling has already taken place)

After a punching or punch-nibbling step, a perforated initial shape 5 is present, cf. FIG. 5. This has punched apertures 4, as shown schematically in FIG. 5. After cutting I and punching II, the sheet metal shows in practice certain internal stress which leads to deformation of the initial shape 5. Consequently, rolling III has to be carried out, which rolls/smoothes the sheet metal to obtain a perforated plane 6. In top view, the initial shape 5 cannot be distinguished from the perforated plane 6, which is why both reference signs were used in FIG. 5.

Furthermore, FIG. 5 shows the inner portion 7 and the edge portions 8. These are preferably punched with different tools so that they have different perforations.

The subject matter of the embossing V according to the invention, which produces the desired three-dimensional structure in the manner of a meshwork imitation, is exclusively the inner portion 7 or the inner portion 7 and the edge portions 8.

Figure 6:
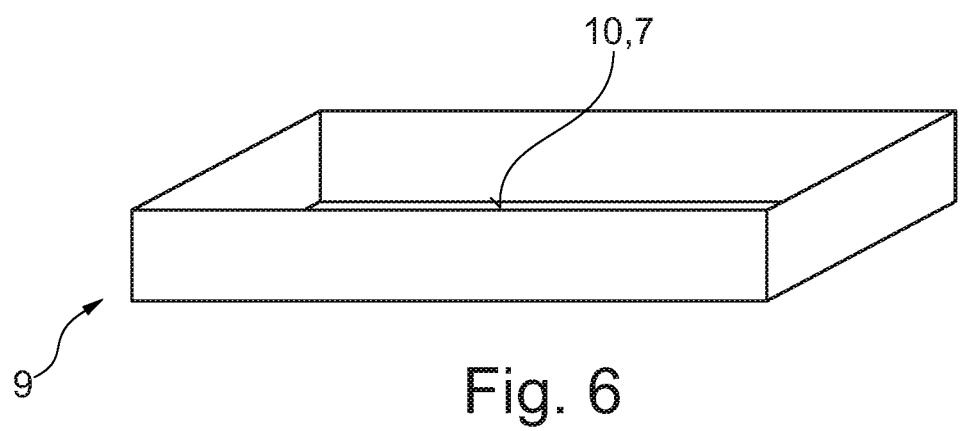
FIG. 6 shows a sieve basket shape after bending.

After bending IV, a sieve basket shape 9 is obtained (cf. FIG. 6). A raw bottom 10 corresponds to the inner portion 7. As soon as embossing V has been carried out, the (flat) raw bottom 10 shows the corrugations according to the invention (cf. FIGS. 9, 10).

Figure 8:
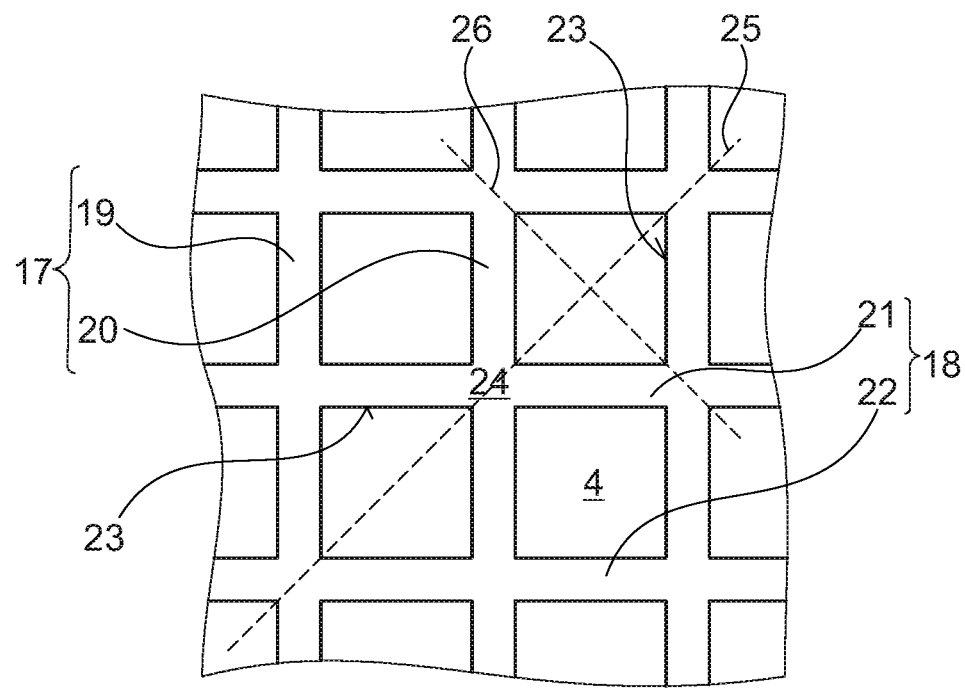
FIG. 8 shows the area in FIG. 7 indicated by viii schematically enlarged.

FIG. 7 shows a sieve basket 1 for holding items to be cleaned, having a plurality of apertures 4 as also shown in the detailed view in FIG. 8. The sieve basket 1 has in the present case a rectangular base surface/base plane with a three-dimensionally structured bottom 11 from which side walls 4 extend from each side edge, i.e. four side walls 4 in the present case.

Figure 9:
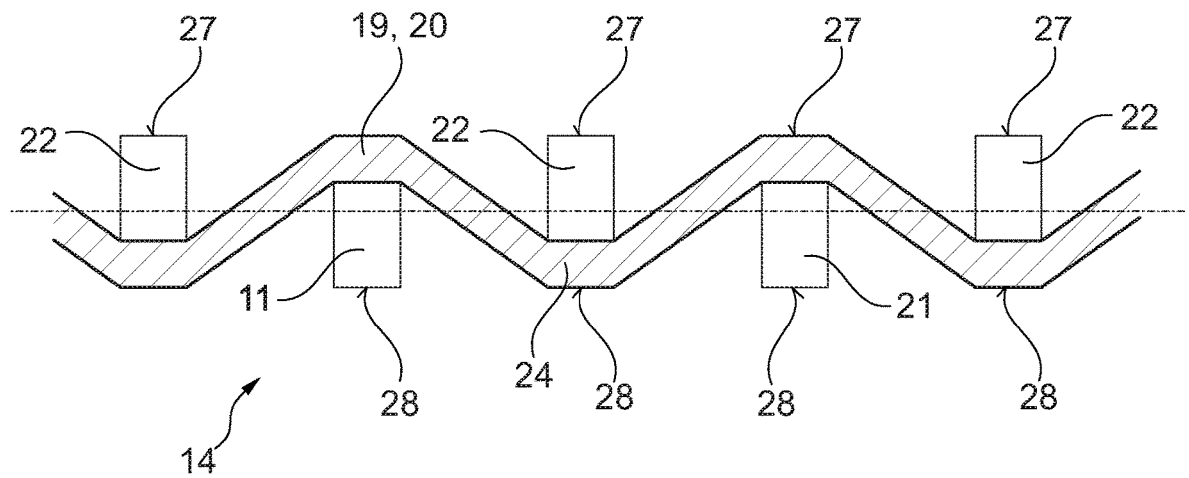
FIG. 9 shows the area in FIG. 7 indicated by ix schematically enlarged.

The bottom 11, as can be seen in the detailed view in FIG. 9, has periodic corrugations or indentations 14. These corrugations 14 project from the base plane towards the sieve basket interior 15 and in the present case also towards the sieve basket exterior 16, so that the sheet metal part/the bottom 11 adopts the meshwork structure surface.

According to the detailed view in FIG. 8, which shows a top view of a section of the bottom 11, the bottom 11 has a grid structure in the projection. This is composed of a plurality of longitudinal strut pairs 17 (also called longitudinal web pairs) and transverse strut pairs 18 (also called transverse web pairs) running parallel in the base plane, i.e. in the present top view.

A single longitudinal strut pair 17 is composed of two longitudinal struts 19, 20. These longitudinal struts 19, 20 run parallel to each other in the base plane, i.e. in the present top view. A spatial view (cf. FIGS. 9 and 10) shows that each strut 19, 20 has a different, approximately complementary geometry in the third spatial direction, i.e. towards the sieve basket interior 15 and/or towards the sieve basket exterior 16.

A single transverse strut pair 18 is composed of two transverse struts 21, 22. These transverse struts 21, 22 run parallel to each other in the base plane, i.e. in the present top view. A spatial view (cf. FIGS. 9 and 10) shows that each strut 21, 22 has a different, approximately complementary geometry in the third spatial direction, i.e. towards the sieve basket interior 15 and/or towards the sieve basket exterior 16.

The surface spanned by the apertures 4 fulfils two different functions. Firstly, it provides a contact and fixation surface 23 on the edge surface of each strut 19 to 22 facing the aperture 4. This surface 23 increases with the size of the apertures 4. The larger the items to be inserted are, the larger the apertures 4 have to be designed in order to ensure that there is enough contact and fixation surface 23. Secondly, the surface spanned by the apertures 4 allows the cleaning liquid to drip out of the sieve basket 1. The drip-off function also increases with the size of the apertures 4. Accordingly, this second function also encourages the surface ratio between the strut pairs 17, 18 and the surface of the apertures 4 to be kept smaller than 1. A maximum is set for the surface area spanned by the apertures 4 in that it has to be small enough to prevent devices to be cleaned from falling out.

The grid structure defined by the bottom 11 has bottom nodes 24 resulting from the embossing V. According to the invention, these bottom nodes 24 do not lie in the same plane, because the corrugations 14 are formed. A particular advantage of the invention is that the bottom nodes 24, which are each formed by intersecting a longitudinal strut 19, 20 with a transverse strut 21, 22, have approximately the same material thickness as the respective longitudinal or transverse strut 19 to 22.

The meshwork simulation according to the invention not only allows the imitation of a meshwork, but also has the advantage over a meshwork that there is no overlap in the area of the node 24, i.e. no doubling of the material thickness, but there is the same constant material thickness as in the rest of the bottom. Before this feature is dealt with further in connection with FIG. 9, two further parameters of the present invention are introduced.

In this way, a part of the bottom nodes 24 can be hypothetically connected to each other to identify the first hypothetical connection line 25. As can be seen in the following, the bottom nodes 24 connected by the first hypothetical connection line 25 represent bottom nodes 24 which, in accordance with an advantageous configuration of the invention, are each arranged at the same height and project into the sieve basket interior 15. They each constitute, so to speak, a wave crest 27 (see FIG. 9) of the periodic corrugations 14.

In the base plane rotated by 90°, a second hypothetical connection line 26 can be seen next to line 25. This results from connecting the bottom nodes 24 left out by the first hypothetical connection line 25. As can be seen in the following, the bottom nodes 24 connected by the second hypothetical connection line 26 represent bottom nodes 24 which, in accordance with an advantageous configuration of the invention, are each arranged at the same height and project towards the sieve basket exterior 16. They each constitute, so to speak, a wave trough 28 (see FIG. 9) of the periodic corrugations 14.

These wave crests 27 and wave troughs 28 are shown in FIG. 9. FIG. 9 shows a sectional drawing through the bottom 11 (cf. section ix of FIG. 7). The strut shown here is a longitudinal strut 19, 20 which, however, does not differ structurally from a transverse strut 21, 22 in its basic form. From the visible edges it can be seen that a first transverse strut 21 starts from each wave crest 27 of the longitudinal strut 19, 20, while a second transverse strut 22 starts from each wave trough 28. The reciprocity of the wave crest 27 and wave troughs 28 described above can be clearly seen here.

The longitudinal strut 19, 20 has an angular course in the present case. However, this shape is only of exemplary character. In other configurations, in particular an approximately sinusoidal waveform is desired.

FIG. 9 furthermore shows that the material thickness of the bottom node 24 does not exceed that of the remaining longitudinal strut 19, 20, which means that despite the meshwork simulation there is no disadvantageous overlapping of the struts as described above.

Figure 10:
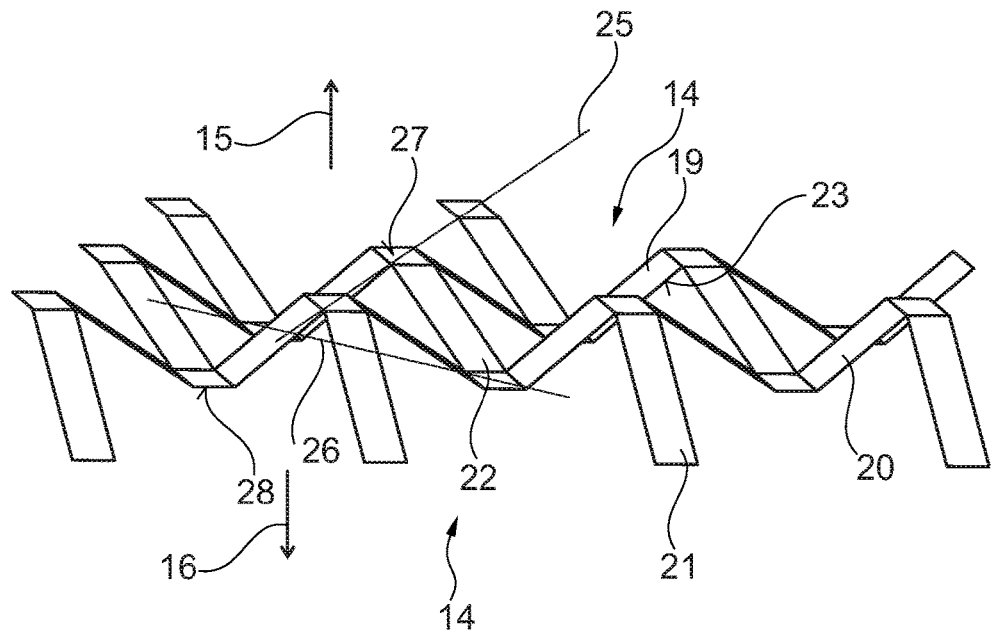
FIG. 10 shows a perspective view of a meshwork-imitated bottom.

In FIG. 10, the corrugations 14 are shown in perspective. The first hypothetical connection line 25 (cf. FIG. 8) connects the wave crests 27, the second hypothetical connection line 26 (cf. FIG. 8) connects the wave troughs 28. The three-dimensional roof shape formed between four adjacent bottom nodes 24 is made up of two triangles. The apex of these triangles can be placed, depending on the viewpoint, between the two wave crests 27 of the four adjacent bottom nodes 24 (then the roof is closed towards the sieve basket interior 15) or between the two wave troughs 28 of the four adjacent bottom nodes 24 (then the roof is open towards the sieve basket interior and closed towards the sieve basket exterior 16).

FIG. 10 shows that the structure formed by the embossing V, which shows a rectangular grid structure in the projected plan view from FIG. 8, has a high degree of three-dimensionality in perspective, which reduces the moistening of this surface with droplets after removal from the CDD. In addition, the structure created by the corrugations 14 provides sufficiently large contact and fixation surfaces 23.

Figure 11:
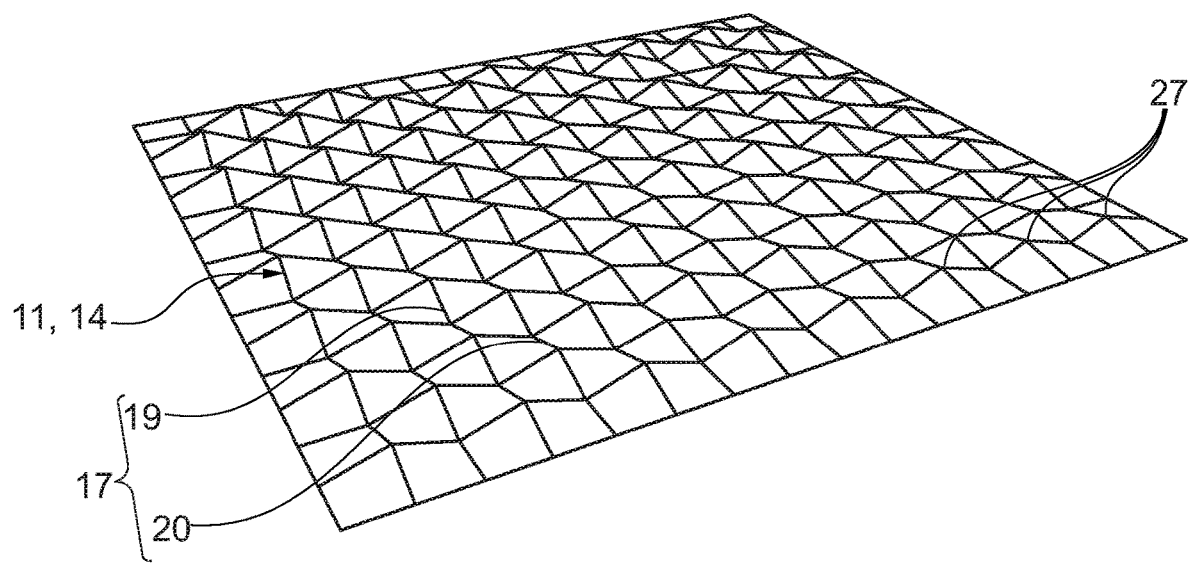
FIG. 11 shows a perspective view of a further configuration of the meshwork-imitated bottom.

FIG. 11 shows the three-dimensional corrugations 14 as well as the fluting caused by them in a further section. There are so many corrugations 14 arranged over the entire surface of the bottom 11 that the total number of wave crests 27 and wave troughs 28 gives the user the impression of an approximately flat surface. According to the invention, the advantages of a flat surface (such as the unproblematic placement of the sieve basket) are thus realized while avoiding its disadvantages (see above).

Figure 12:
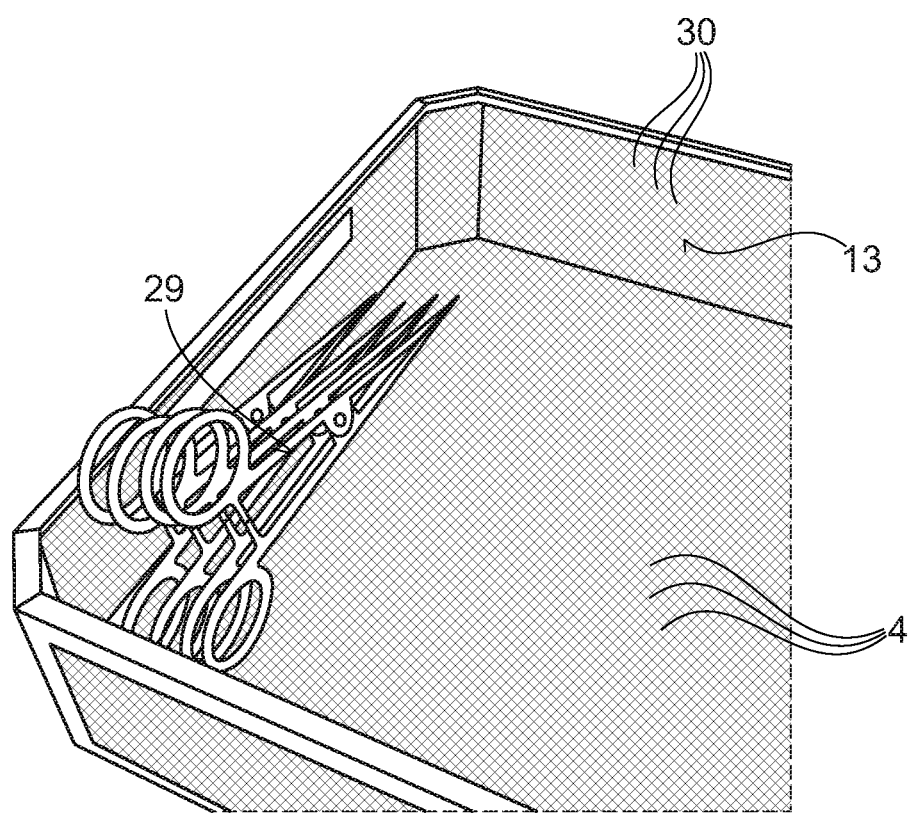
FIG. 12 shows a section of the sieve basket with inserted items.

FIG. 12 shows a section of a sieve basket 1. Several items 29, in the present case surgical scissors, are arranged in this basket, which remain in position due to the corrugations 14 and due to the contact and fixation surfaces 23 created by them. The sieve basket 1 has side walls 13 in addition to the bottom 11. These also have apertures 30, which differ geometrically from those in the bottom 11. In the present case, the apertures 30 are more finely meshed than the apertures 4, so that in such a case, in which the items 29 slide towards the side wall 13, there is no danger of pointed sections of the items 29 projecting sideways. Furthermore, the side walls 13 are designed to be smooth, i.e. explicitly not corrugated.

The invention claimed is:

1. A method for producing a sieve basket for receiving medical items to be disinfected or sterilized, the method comprising the steps of:
   in a first processing step, producing a base plate or sieve basket base surface comprising a bottom and side walls of the sieve basket in one piece;
   in a second processing step taking place prior to or after the first processing step, providing the base plate or the sieve basket base surface with apertures or holes in order to obtain a perforated initial shape;
   in a third processing step taking place after the first and second processing steps, flattening the base plate or sieve basket base surface to remove warping caused by internal stresses that develop after the first processing step and/or the second processing step, producing a perforated or punched plane that is divided into a flat inner portion and edge portions;
   in a fourth processing step taking place after the third processing step, producing a sieve basket shape with a raw bottom and side walls extending vertically thereto, the raw bottom corresponding to the flat inner portion and the side walls corresponding to the flat edge portions of the perforated or punched plane; and
   in a fifth processing step, which takes place directly or indirectly after the third processing step, embossing the flat inner portion with at least one embossing punch, pressing the at least one embossing punch by a press onto the flat inner portion in such a way that the flat inner portion plastically adapts to the negative shape of the at least one embossing punch so that an entirety of the flat inner portion forms a three-dimensionally structured bottom.

2. The method according to claim 1, wherein the fifth processing step takes place prior to the fourth processing step.

3. The method according to claim 1, wherein the first, second, third, fourth and fifth processing steps are done in chronological order.

4. The method according to claim 1, wherein, after the fourth processing step, a sixth processing step takes place, which connects the edge portions together, which now constitute the side walls of the sieve basket.

5. The method according to claim 1, wherein the apertures obtained in the second processing step cause perforations which are structured differently from each other in the flat inner portion and the edge portions.

6. The method according to claim 1, wherein the at least one embossing punch comprises a plurality of punches, and wherein the plurality of punches is used so that the flat inner portion comprises the three-dimensionally structured bottom.

7. The method according to claim 6, wherein the at least one embossing punch is designed in such a way that the three-dimensionally structured bottom has corrugations or indentations which project towards a sieve basket interior and/or towards a sieve basket exterior, so that the three-dimensionally structured bottom has a surface comprising a meshwork.

8. The method according to claim 6, wherein the at least one embossing punch is designed in such a way that the three-dimensionally structured bottom comprises a plurality of longitudinal strut pairs and a plurality of transverse strut pairs that run perpendicular to the plurality of longitudinal strut pairs in a top view of the three-dimensionally structured bottom.

9. The method according to claim 6, wherein the at least one embossing punch is designed in such a way that the three-dimensionally structured bottom forms contact and fixing surfaces for items to be inserted into the sieve basket.

10. The method according to claim 1, wherein the first processing step comprises a cutting step.

11. The method according to claim 1, wherein the second processing step comprises a punching step.

12. The method according to claim 1, wherein the third processing step comprises a rolling step to remove said warping caused by internal stresses that develop after the first processing step and/or the second processing step.

13. The method according to claim 1, wherein the fourth processing step comprises a bending step.

14. The method according to claim 1, wherein the three-dimensionally structured bottom consists of a plurality of longitudinal struts and a plurality of transverse struts that intersect the plurality of longitudinal struts in nodes, forming alternating wave crests and wave troughs, wherein the wave crests are arranged in a first plane and the wave troughs are arranged in a second plane parallel to and offset from the first plane.

15. A method for producing a sieve basket for receiving medical items to be disinfected or sterilized, the method comprising the steps of:
    producing a base plate from a sheet metal blank, the base plate comprising an inner portion and edge portions;
    forming apertures in the inner portion to create a plurality of struts;
    processing the base plate to remove warping caused by internal stresses that develop after the step of producing the base plate and/or the step of forming apertures, so that the inner portion and edge portions are flat and conform to a single plane;
    bending or deforming the edge portions relative to the inner portion to form a sieve basket shape having a bottom and sidewalls; and
    pressing at least one embossing punch onto the inner portion, after the step of processing the base plate to remove warping, to plastically deform the plurality of struts so that each strut assumes a uniform wave shape.

16. The method according to claim 15, wherein the plurality of struts form a plurality of nodes.

17. The method according to claim 16, wherein the plurality of struts further comprise a plurality of longitudinal struts and a plurality of transverse struts that intersect the plurality of longitudinal struts at the nodes.

18. The method according to claim 17, wherein the plurality of longitudinal struts are perpendicular to the plurality of transverse struts.

19. The method according to claim 16, wherein the step of pressing at least one embossing punch onto the inner portion to plastically deform the plurality of struts comprises plastically deforming each strut so that a first subset of the plurality of nodes form wave crests and a second subset of the plurality of nodes form wave troughs.

20. The method according to claim 15, wherein the uniform wave shape is a trapezoidal shape.

21. The method according to claim 15, wherein the steps are performed in chronological order.

* * * * *